United States Patent
Wolff

(10) Patent No.: US 12,226,323 B2
(45) Date of Patent: Feb. 18, 2025

(54) FLOATING CLAMP FOR SPINAL SURGERIES

(71) Applicant: Spineology Inc., St. Paul, MN (US)

(72) Inventor: Kyle Wolff, St. Paul Park, MN (US)

(73) Assignee: Spineology Inc., St. Paul, MN (US)

( * ) Notice: Subject to any disclaimer, the term of this patent is extended or adjusted under 35 U.S.C. 154(b) by 0 days.

(21) Appl. No.: 17/960,797

(22) Filed: Oct. 5, 2022

(65) Prior Publication Data

US 2023/0107280 A1    Apr. 6, 2023

Related U.S. Application Data

(60) Provisional application No. 63/252,331, filed on Oct. 5, 2021.

(51) Int. Cl.
*A61F 2/46* (2006.01)

(52) U.S. Cl.
CPC ................. *A61F 2/4611* (2013.01)

(58) Field of Classification Search
CPC ............... A61F 2/4611; A61B 17/6416; A61B 17/6458; A61B 17/6466; F16B 2/065; F16B 2/12

See application file for complete search history.

(56) References Cited

U.S. PATENT DOCUMENTS

| | | | |
|---|---|---|---|
| 6,464,634 B1 | 10/2002 | Fraser | |
| 11,065,131 B2 | 7/2021 | Boylan et al. | |
| 2002/0151892 A1* | 10/2002 | Walulik | A61B 17/66 606/57 |
| 2004/0186346 A1 | 9/2004 | Smith et al. | |
| 2007/0161983 A1* | 7/2007 | Cresina | A61B 17/66 606/54 |
| 2008/0221394 A1 | 9/2008 | Melkent et al. | |
| 2009/0275952 A1 | 11/2009 | Lawson et al. | |
| 2012/0150182 A1* | 6/2012 | Dominik | A61B 17/60 606/59 |
| 2013/0289354 A1 | 10/2013 | Ainsworth et al. | |
| 2014/0303666 A1 | 10/2014 | Heiman et al. | |
| 2017/0340358 A1 | 11/2017 | Bullard | |
| 2019/0091038 A1 | 3/2019 | Boylan et al. | |
| 2020/0397481 A1* | 12/2020 | Samchukov | A61B 17/6416 |

* cited by examiner

*Primary Examiner* — Julianna N Harvey
*Assistant Examiner* — Angel Roberto Mora-Velazquez
(74) *Attorney, Agent, or Firm* — Skaar Ulbrich Macari, P.A.

(57) ABSTRACT

A floating clamp for surgical procedures includes a clamp body and a spring mechanism to allow in/out movement of a portal tube, while maintaining the tube's position in A/P and C/C. The clamp body includes a base portion and an arm pivotally coupled to the base portion such that a distal end of the arm pivots towards and away from a distal end of the base portion. The spring mechanism includes a coil spring and a piston disposed through the coil spring. The spring mechanism can be coupled to the clamp body adjacent to a proximal end thereof.

20 Claims, 5 Drawing Sheets

FLOATING CLAMP FOR SPINAL SURGERIES

PRIORITY

This application claims the benefit of U.S. Provisional Application Ser. No. 63/252,331, filed on Oct. 5, 2021, which is hereby incorporated herein by reference in its entirety.

FIELD

The present invention generally relates to devices used in orthopedic surgeries, and more particularly to clamping instruments, implants, tools and methods used for spinal surgical procedures such as interbody fusion procedures.

BACKGROUND

In surgical procedures it is desirable to provide instruments, such as a portal tube that allows for convenient access to the patient's anatomy for performing the procedure and for delivering implants, instruments and the like while minimizing trauma to the patient. The portal can be selectably fixed in place by a clamp that secures to the tube. However, conventional portal tube holders do not allow the tube to float with the patient's anatomy. Thus, any spine movement during the surgical procedure could result in separation of the tube and spine.

There is an ongoing need to provide instruments, implants, tools and methods used for spinal surgical procedures such as interbody fusion procedures that improve upon the conventional art as discussed herein.

SUMMARY

Disclosed is a clamp for a portal tube. The clamp is spring-loaded to allow in/out movement of the tube, while maintaining the tube's position in A/P and C/C.

In one example, a floating clamp for surgical procedures includes a clamp body and a spring mechanism to allow in/out movement of a portal tube, while maintaining the tube's position in A/P and C/C. The clamp body includes a base portion and an arm pivotally coupled to the base portion such that a distal end of the arm pivots towards and away from a distal end of the base portion. The spring mechanism includes a coil spring and a piston disposed through the coil spring. The spring mechanism can be coupled to the clamp body adjacent to a proximal end thereof.

The piston can also be disposed through an aperture defined through the base portion of the clamp body. A removable cap can be secured to the piston on a side of the base portion that is opposite a side where the coil spring is located. The piston can include a head that engages the coil spring. The head can have a diameter that is larger than an inner diameter of the coil spring. The head can have a plurality of teeth arrayed about the head.

The piston can define a slot or channel in a longitudinal direction. The floating clamp can include a travel limit pin disposed in the base and protruding into the slot or channel to limit rotational movement of the piston relative to the base.

In an example, a surgical portal system can include a tubular portal and the floating clamp for surgical procedures. The distal end of the arm and the distal end of the body of the clamp can each be configured to grasp and hold securely the tubular portal. A table arm, a support member or a framework can be coupled to the floating clamp.

In an example a method of floating a clamp for a surgical portal can include securing the clamp to the surgical portal, biasing the clamp towards the patient with a coil spring, and moving the clamp away from the patient when a force is applied to the surgical portal sufficient to overcome a biasing force of the coil spring.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
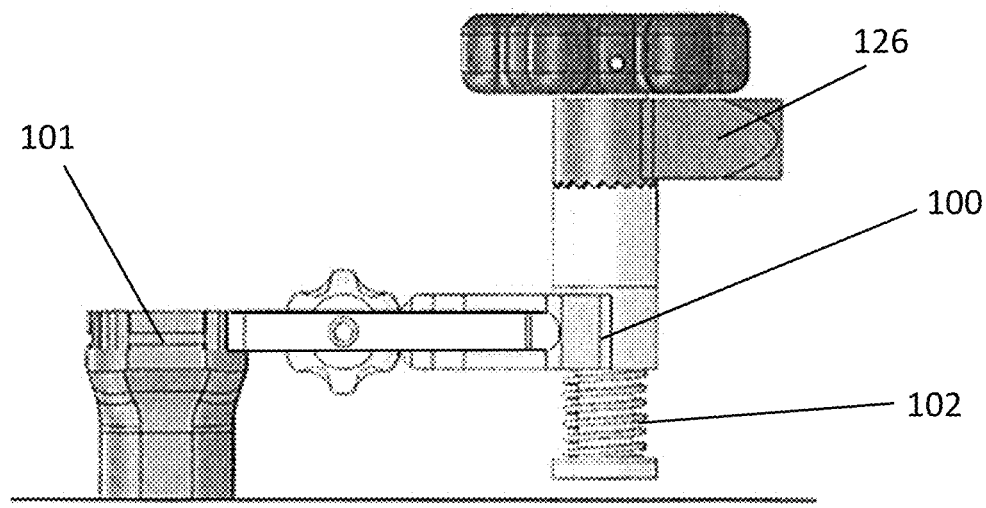
FIG. 1 is a side view of a clamp engaged with a tubular surgical portal in accordance with certain embodiments of the invention.
Figure 2:
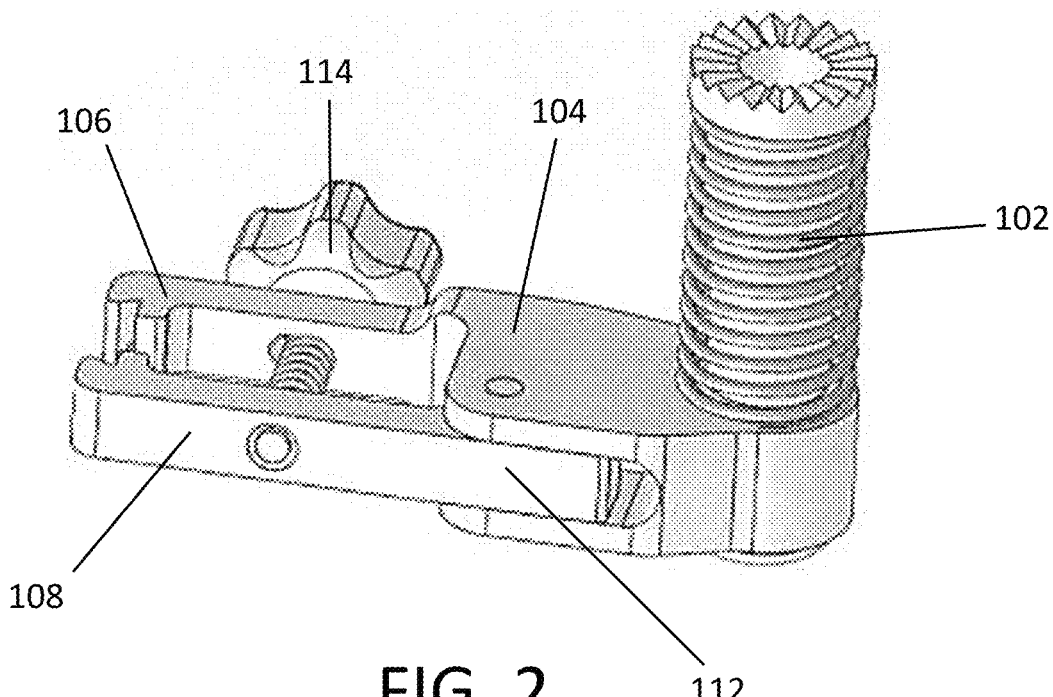
FIG. 2 is a perspective view of a clamp for a tubular surgical portal in accordance with certain embodiments of the invention.
Figure 3:
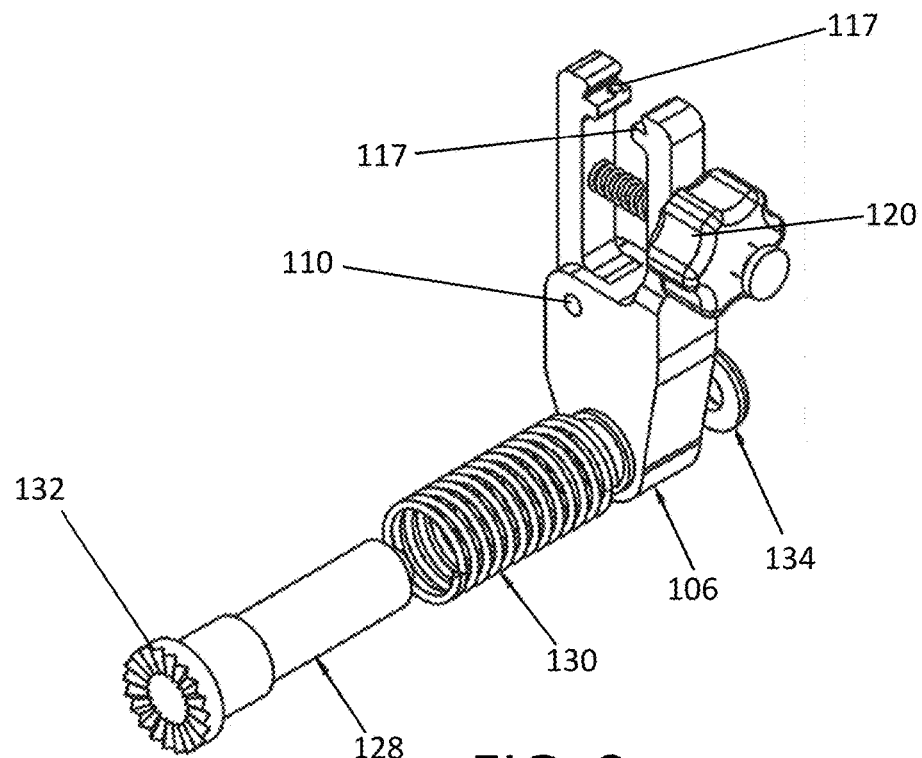
FIG. 3 is a perspective partial exploded view of a clamp for a tubular surgical portal in accordance with certain embodiments of the invention.
Figure 4:
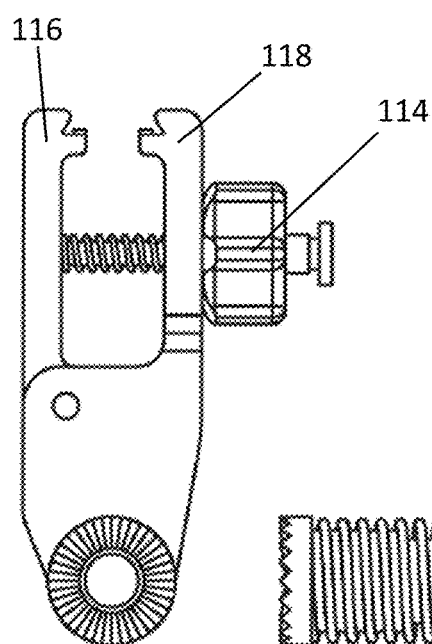
FIG. 4 is a top view of a clamp for a tubular surgical portal in accordance with certain embodiments of the invention.
Figure 5:
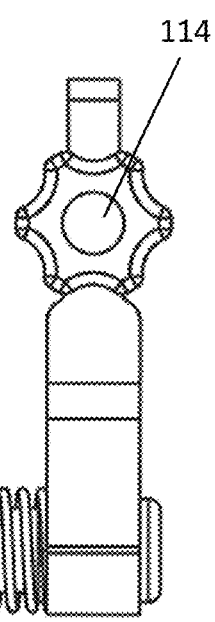
FIG. 5 is a side view of a clamp for a tubular surgical portal in accordance with certain embodiments of the invention.
Figure 6:
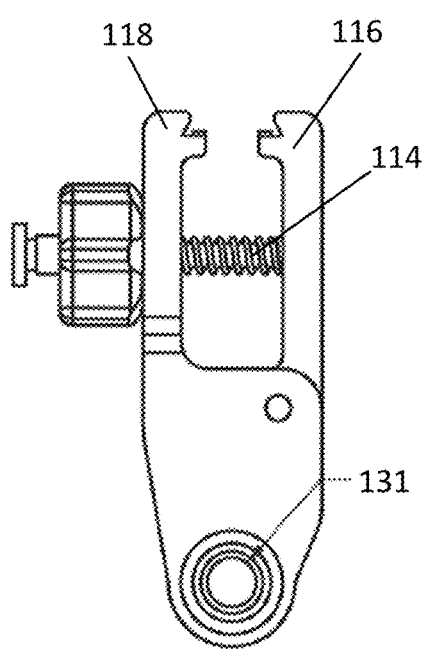
FIG. 6 is a bottom view of a clamp for a tubular surgical portal in accordance with certain embodiments of the invention.
Figure 7:
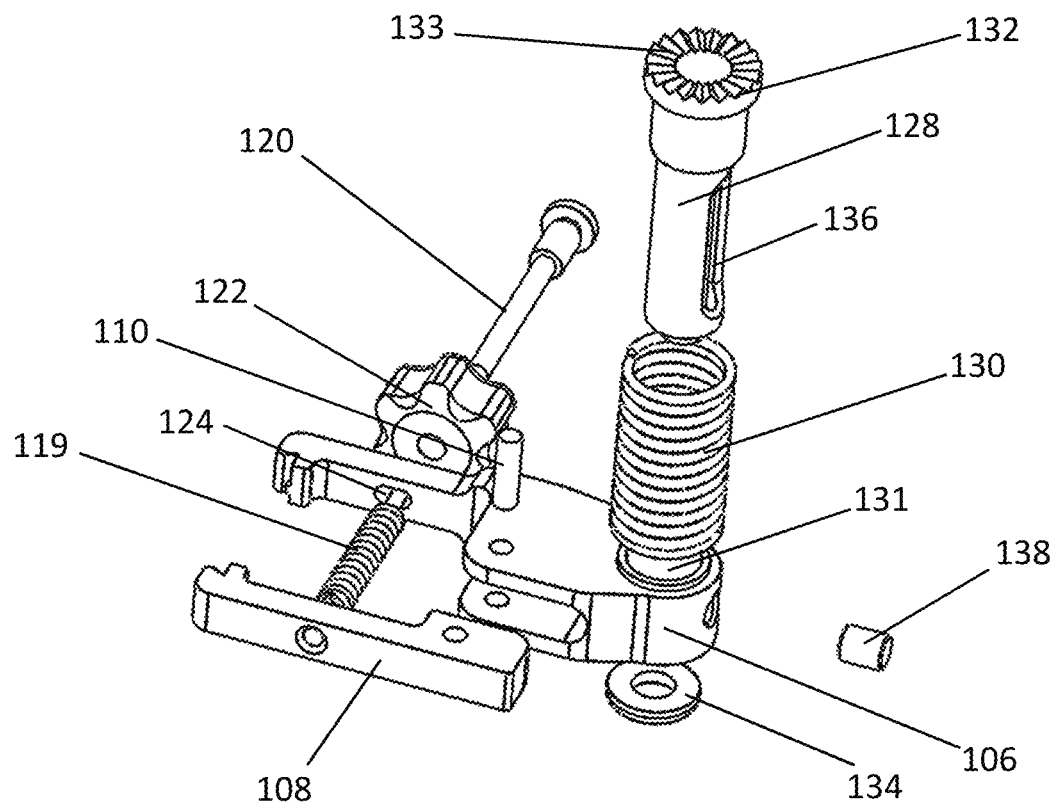
FIG. 7 is a perspective exploded view of a clamp for a tubular surgical portal in accordance with certain embodiments of the invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the spirit and scope of the invention as defined by the appended claims. For illustrative purposes, cross-hatching, dashing or shading in the figures is provided to demonstrate sealed portions and/or integrated regions or devices for the package.

DETAILED DESCRIPTION

In the following descriptions, the present invention will be explained with reference to example embodiments thereof. However, these embodiments are not intended to limit the present invention to any specific example, embodiment, environment, applications or particular implementations described in these embodiments. Therefore, description of these embodiments is only for purpose of illustration rather than to limit the present invention. It should be appreciated that, in the following embodiments and the attached drawings, dimensional relationships among individual elements in the attached drawings are illustrated only for ease of understanding, but not to limit the actual scale unless specifically claimed as such.

Referring to FIG. 1, a floating surgical clamp 100 is configured to be joined to a surgical portal tube 101. The clamp 100 includes a spring mechanism 102 to allow the clamp, and thus the portal tube 101, to move upwardly against the spring's bias force.

The floating surgical clamp 100 of the present invention improves upon the clamp disclosed in U.S. Pat. No. 11,065,131 by being spring-loaded to allow in/out movement of the tube, while maintaining the tube's position in A/P and C/C. This is especially helpful in prone cases when the contralateral side of the patient is not supported, which can cause the spine to push away from the tube. The floating clamp 100 uses the spring-loaded mechanism 102 to maintain intimate contact between the surgical tube 101 and patient's anatomy. U.S. Pat. No. 11,065,131 is hereby incorporated by reference herein in its entirety.

Referring to FIGS. 1-9, the surgical clamp 100 generally comprises a clamp body 104 and a spring mechanism 102. The clamp body comprises a base portion 106 and a pivoting arm 108. The pivoting arm 108 pivots about a pin 110 securing a proximal end 112 of the arm 108 to the base 106. An adjustment mechanism 114 is coupled to the arm 108 to change its pivot angle. Changing the pivot angle brings the distal end 116 of the arm 108 towards or away from a respective distal end 118 of the base 106. The respective distal ends 116, 118 are configured to grasp, interlock or mate with corresponding features on the portal tube 101. For example, the distal ends 116, 118 define grooves 117 that mate with corresponding dovetail features defined in an outer surface of a wall of the surgical portal 101.

The adjustment mechanism 114 comprises a spring 119 disposed between the arm 108 and base 106. A shaft 120 is inserted through a thumb nut or wheel 122 and an aperture 124 defined through the arm and through the spring. The distal end of the shaft 120 is secured into the base 106. The wheel 124 is turned on a first direction to tighten or pivot the arm 108 towards the base 106 to secure the surgical tube 101 to the clamp 100. The wheel 124 is turned in the second or opposite direction to release the force securing the surgical tube 101 to the clamp 100.

The clamp 100 may attach to a table arm, support member 126, framework or other mechanism or structure on or in the operating room. For example, the clamp in FIG. 1 is attached to a support arm 126.

The spring mechanism 102 comprises a cylindrical piston 128 that is disposed through a coil spring 130 and an aperture 131 through a proximal portion of the clamp base portion 106. The piston 128 has a head 132 with a larger diameter than the inner diameter of the spring 130 so that the piston does not pass through the spring 130 from a first direction. A removable cap 134 is attached to the opposing second end of the piston 128 to keep the piston from passing through the clamp base 106 and spring 130 from a second direction, opposite the first direction.

A slot 136 or channel is defined laterally through a portion of the longitudinal length of the piston. When the piston 128 is inserted through the aperture 131 in the base 106, a travel limit pin 138 is inserted into the base 106 so that it protrudes into the channel or slot 136 to limit the extent of vertical travel of the piston 128 relative to the base 106. The travel limit pin 138 engaging the channel or slot 136 also prevents the piston from rotating relative to the base 106.

The upper surface of the head 132 can be provided with a series of teeth 133 to engage a corresponding series of teeth in a fixture or support structure 126. The engagement of the teeth prevent the clamp from unintentionally rotating about the longitudinal axis of the piston with respect to the fixture or support structure 126.

Figure 8:
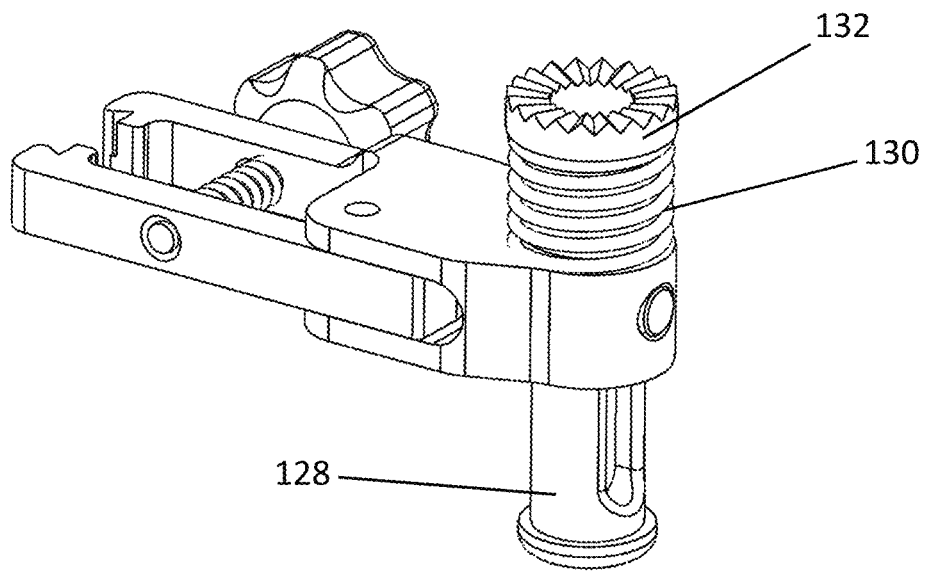
FIG. 8 is a perspective view of a clamp for a tubular surgical portal at a first end limit of travel in accordance with certain embodiments of the invention.
Figure 9:
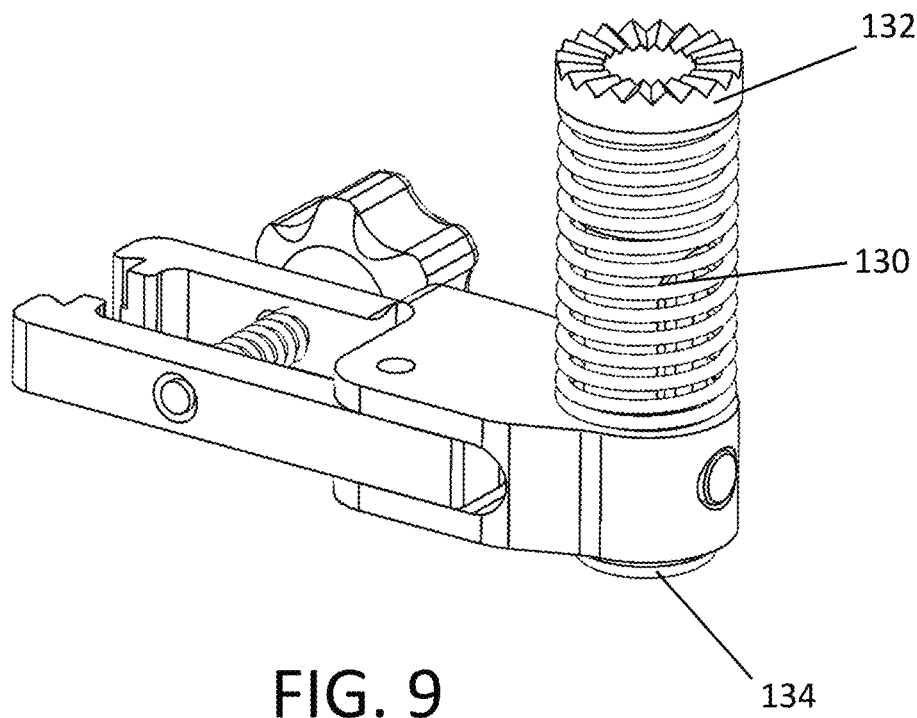
FIG. 9 is a perspective view of a clamp for a tubular surgical portal at an opposing second end limit of travel in accordance with certain embodiments of the invention.

Referring to FIGS. 8-9, the clamp assembly 100 is first shown in FIG. 8 at its upper limit of travel. The spring 130 is the most compressed in this view. The clamp 100 is then shown in its opposing most-relaxed position for the spring 130 in FIG. 9, which is most downward. However, there is still some force applied in this second position to maintain some downward force for the tubular portal towards the patient's anatomy. The clamp 100 can float between these two endpoints as needed to accommodate movement of the spine during the surgical procedure. The spring's force can be set according to the surgeon's preferences by changing the spring or by adjusting preload on the spring such as with a preload spacer or adjustable collar. Spacers can be added to either or both ends of the spring shaft to limit travel as desired.

In use, the floating clamp 100 in certain embodiments allows the portal tube 101 and fixation pin to move up and down in a piston-like manner with the spine via a spring mechanism 102 if the spine moves away from the portal tube during the surgical procedure. Otherwise, such movement can result in the fixation pin pulling out and the portal tube migrating. The floating clamp advantageously maintains orientation of the portal tube 101 in the medial/lateral and cephalad/caudal planes. The clamp 100 can be adapted to a variety of sizes of portal tubes.

Figure 10:
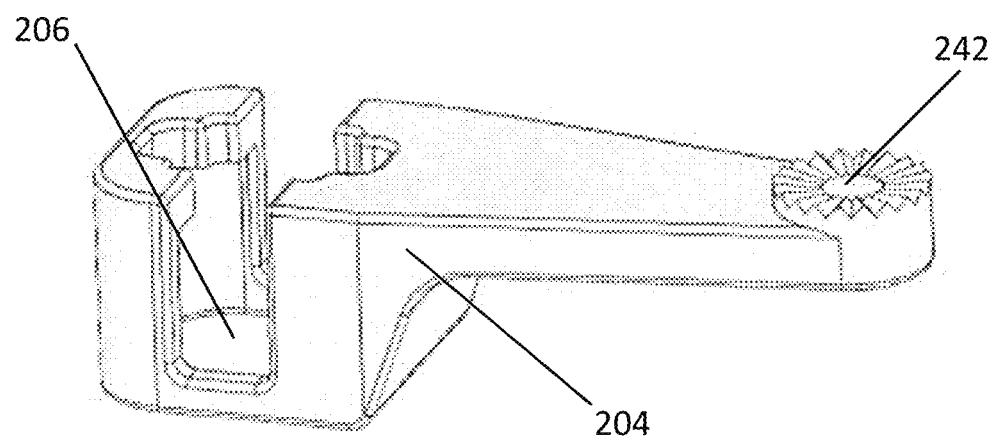
FIG. 10 is a perspective view of a clamp for a tubular surgical portal in accordance with certain embodiments of the invention.

FIG. 10 illustrates an alternative embodiment of a clamp body 204 to the base and arm of the clamp body described above. Here, the body 204 is a single piece without a pivoting arm. The distal end defines an aperture 206 that is sized and shaped to securely hold a corresponding particular shape and size of surgical portal tube. Changing the portal tube size or configuration requires changing the body 204 to a different body with the correct corresponding shape and size.

Figure 11:
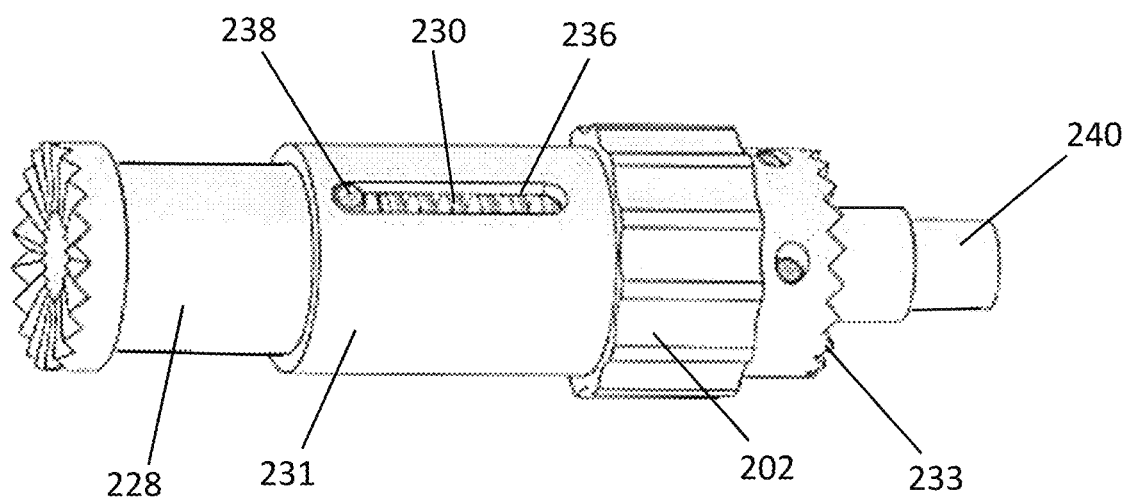
FIG. 11 is a perspective view of a clamp for a tubular surgical portal in accordance with certain embodiments of the invention.

FIG. 11 illustrates an alternative embodiment of a spring mechanism 202. In this embodiment, the spring 230 is enclosed inside of a hollow tube 231. A piston 228 moves longitudinally within the interior of the tube 231 against the spring 230. A pin 238 engages an opposing pair of slots 236 in the tube's sidewall to prevent rotation and to limit the travel of the piston 228 with respect to the tube 231. A bottom post 240 extends below the tube 231 to fit into a respective aperture 242 defined in the body, such as shown in FIG. 10. Opposing sets of teeth defined on the bottom collar of the tube 233 and the top surface surrounding the aperture 242 on the body 204 (as well as the teeth on the head 232 of the piston 228) prevent the clamp from unintentionally rotating about the longitudinal axis of the piston with respect to the fixture or support structure.

The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiment described herein which equivalents are intended to be encompassed by the claims attached hereto.

What is claimed is:

1. A floating clamp for surgical procedures, comprising:
   a clamp body, comprising:
      a base portion; and
      an arm pivotally coupled to the base portion such that a distal end of the arm pivots towards and away from a distal end of the base portion about a pivot axis; and
   a spring mechanism coupled to the clamp body, the spring mechanism comprising:
      a coil spring; and
      a piston disposed through the coil spring such that a longitudinal axis of the piston is oriented substantially parallel to the pivot axis of the arm of the clamp body,
   wherein the spring mechanism is coupled to the clamp body adjacent to a proximal end thereof.

2. The floating clamp for surgical procedures of claim 1, wherein the piston is also disposed through an aperture defined through the base portion of the clamp body, wherein the aperture is oriented substantially parallel to the pivot axis.

3. The floating clamp for surgical procedures of claim 2, wherein a removable cap is secured to the piston on a side of the base portion that is opposite a side where the coil spring is located.

4. The floating clamp for surgical procedures of claim 3, wherein the piston comprises a head that engages the coil spring, wherein the head has a diameter that is larger than an inner diameter of the coil spring.

5. The floating clamp for surgical procedures of claim 1, wherein the piston comprises a head that engages the coil spring, wherein the head has a diameter that is larger than an inner diameter of the coil spring.

6. The floating clamp for surgical procedures of claim 5, wherein the head comprises a plurality of teeth arrayed about the head.

7. The floating clamp for surgical procedures of claim 1, wherein the piston defines a slot or channel in a longitudinal direction, and the floating clamp for surgical procedures further comprises a travel limit pin disposed in the base portion and protruding into the slot or channel to limit rotational movement of the piston relative to the base portion.

8. The floating clamp for surgical procedures of claim 1, wherein the clamp body comprises an adjustment mechanism to adjust a pivot angle of the arm, wherein the adjustment mechanism is separate from the spring mechanism.

9. The floating clamp for surgical procedures of claim 8, wherein the adjustment mechanism comprises:
   a second spring disposed between the base portion and the arm;
   a shaft disposed through the second spring, a first aperture defined in the base portion and a second aperture defined in the arm; and
   an adjustment nut or wheel coupled to an end of the shaft.

10. A surgical portal system, comprising: a tubular portal; and the floating clamp for surgical procedures according to claim 1, wherein the distal end of the arm and the distal end of the clamp body are each configured to grasp and hold securely the tubular portal.

11. The surgical portal system of claim 10, further comprising a table arm, a support member or a framework coupled to the floating clamp for surgical procedures.

12. A floating clamp for surgical procedures, comprising:
   a clamp body, comprising:
      a base portion; and
      an arm pivotally coupled to the base portion such that a distal end of the arm pivots towards and away from a distal end of the base portion; and
   a spring mechanism coupled to the clamp body, the spring mechanism comprising:
      a coil spring; and
      a piston disposed through the coil spring,
   wherein the spring mechanism is coupled to the clamp body adjacent to a proximal end thereof such that the arm can pivot in a first plane independently of the clamp body moving in a second plane substantially perpendicular to the first plane via the spring mechanism.

13. The floating clamp for surgical procedures of claim 12, wherein the clamp body comprises an adjustment mechanism to adjust a pivot angle of the arm, wherein the adjustment mechanism is separate from the spring mechanism.

14. The floating clamp for surgical procedures of claim 13, wherein the adjustment mechanism comprises:
   a second spring disposed between the base portion and the arm;
   a shaft disposed through the second spring, a first aperture defined in the base portion and a second aperture defined in the arm; and
   an adjustment nut or wheel coupled to an end of the shaft.

15. The floating clamp for surgical procedures of claim 12, wherein the piston is also disposed through an aperture defined through the base portion of the clamp body, wherein the aperture is oriented substantially parallel to the pivot axis.

16. The floating clamp for surgical procedures of claim 15, wherein a removable cap is secured to the piston on a side of the base portion that is opposite a side where the coil spring is located.

17. The floating clamp for surgical procedures of claim 16, wherein the piston comprises a head that engages the coil spring, wherein the head has a diameter that is larger than an inner diameter of the coil spring.

18. The floating clamp for surgical procedures of claim 12, wherein the piston comprises a head that engages the coil spring, wherein the head has a diameter that is larger than an inner diameter of the coil spring.

19. The floating clamp for surgical procedures of claim 18, wherein the head comprises a plurality of teeth arrayed about the head.

20. The floating clamp for surgical procedures of claim 12, wherein the piston defines a slot or channel in a longitudinal direction, and the floating clamp for surgical procedures further comprises a travel limit pin disposed in the base portion and protruding into the slot or channel to limit rotational movement of the piston relative to the base portion.

* * * * *